US012594093B2

(12) United States Patent
Tada et al.

(10) Patent No.: US 12,594,093 B2
(45) Date of Patent: Apr. 7, 2026

(54) MEDICAL DEVICE CONTROL APPARATUS AND MEDICAL DEVICE

(71) Applicant: TERUMO KABUSHIKI KAISHA, Tokyo (JP)

(72) Inventors: Yuichi Tada, Santa Clara, CA (US); Yoichiro Kuwano, Machida Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 522 days.

(21) Appl. No.: 18/160,230

(22) Filed: Jan. 26, 2023

(65) Prior Publication Data

US 2023/0240708 A1 Aug. 3, 2023

(30) Foreign Application Priority Data

Jan. 28, 2022 (JP) ................................. 2022-012090

(51) Int. Cl.
*A61B 17/3207* (2006.01)
*A61B 90/00* (2016.01)
*A61B 17/00* (2006.01)

(52) U.S. Cl.
CPC ...... *A61B 17/320758* (2013.01); *A61B 90/06* (2016.02); *A61B 2017/00115* (2013.01)

(58) Field of Classification Search
CPC .... A61B 17/320758; A61B 17/320725; A61B 17/32075; A61B 17/320783; A61B 2017/22038; A61B 2017/22041; A61B 2017/22094
See application file for complete search history.

(56) References Cited

U.S. PATENT DOCUMENTS

2007/0239140 A1 * 10/2007 Chechelski .... A61B 17/320758
                                                              606/1
2010/0125276 A1 *  5/2010 Palermo ......... A61B 17/320758
                                                            408/1 R
2010/0292721 A1    11/2010 Moberg
2020/0054356 A1 *  2/2020 Miller ............ A61B 17/320758

FOREIGN PATENT DOCUMENTS

JP            5281195 A      9/2013

* cited by examiner

*Primary Examiner* — Tuan V Nguyen
(74) *Attorney, Agent, or Firm* — Kim & Stewart LLP

(57) ABSTRACT

A medical device control apparatus for controlling a medical device configured to remove an object in a body cavity with a cutter that is rotatable via a rotatable drive shaft, includes a first motor configured to rotate the drive shaft, one or more sensors configured to detect a state of the first motor, and a controller configured to control the first motor to rotate the drive shaft based on the state of the first motor detected by the one or more sensors.

18 Claims, 4 Drawing Sheets

MEDICAL DEVICE CONTROL APPARATUS AND MEDICAL DEVICE

CROSS-REFERENCE TO RELATED APPLICATION(S)

This application is based on and claims the benefit of priority from Japanese patent application No. 2022-012090, filed Jan. 28, 2022, the entire contents of which are incorporated herein by reference.

BACKGROUND OF THE INVENTION

1. Field of the Invention

Embodiments described herein relate generally to generally to a medical device control apparatus that controls a medical device, and the medical device for removing an object in a body cavity.

2. Description of the Related Art

Examples of treatment methods for a stenosed site caused by plaque, a thrombus, and the like in a blood vessel include a method of dilating the blood vessel by a balloon and a method of indwelling a mesh-like or coil-like stent in the blood vessel as a support for the blood vessel. However, it is difficult by these methods to treat a stenosed site that is hardened due to calcification, and a stenosed site that occurs in a bifurcated portion of the blood vessel. Examples of a method to treat such a stenosed site that is hardened include a method of cutting and removing stenotic objects such as plaque and a thrombus.

As medical devices to be used in this treatment, a medical device provided with a cutting unit that rotates to cut an object in a blood vessel has been known. The medical device provided with the cutting unit includes a drive shaft including the cutting unit in its distal end portion, and a fluid lumen through which the cut object is aspirated. The drive shaft is connected to a rotation drive source such as a motor, and the fluid lumen is connected to a fluid drive source such as a pump.

SUMMARY OF THE INVENTION

Normally, an operator inserts a medical device into a living body, and then manually operates the medical device to perform a rotation operation such as an operation to start or stop the cutting unit. Meanwhile, a medical device control apparatus that automatically controls the operations of the medical device has been developed.

In a case where the operation of the medical device is controlled by the medical device control apparatus, a state of the cutting by the medical device needs to be detected by the medical device control apparatus. The medical device designed to be controlled by the medical device control apparatus is capable of transmitting the operation state of the rotation drive source to the medical device control apparatus. However, in a case of a common medical device without such a configuration, there is a possibility that the medical device control apparatus is unable to detect a state of cutting, and is thus difficult to perform suitable operation control.

Therefore, it is desired that the medical device control apparatus can detect a state of the cutting by the common medical device as well. Moreover, the cutting can be conducted more accurately by collecting information from the medical device in a multifaceted manner. In addition, it is beneficial that the state of the cutting by the medical device can be detected and notified to the operator.

Embodiments of this disclosure provide a medical device control apparatus capable of detecting a state of cutting by a medical device, and the medical device capable of detecting the state of the cutting.

In one embodiment, a medical device control apparatus for controlling a medical device configured to remove an object in a body cavity with a cutter that is rotatable via a rotatable drive shaft, includes a first motor configured to rotate the drive shaft, one or more sensors configured to detect a state of the first motor, and a controller configured to control the first motor to rotate the drive shaft based on the state of the first motor detected by the one or more sensors.

In another embodiment, a medical device for removing an object in a body cavity, includes a rotatable drive shaft, a cutter attached to a distal end of the drive shaft and by which the object is cut, a first motor configured to rotate the drive shaft, one or more sensors configured to detect a state of the first motor, and a controller configured to issue a notification signal based on the state of the first motor detected by the one or more sensors.

In another embodiment, a medical device for removing an object in a body cavity, includes a rotatable drive shaft, a cutter attached to a distal end of the drive shaft and by which the object is cut, a first motor configured to rotate the drive shaft, a microphone configured to collect a sound from the first motor, and a controller configured to control the first motor to rotate the drive shaft based on the sound collected by the microphone.

In another embodiment, a medical device for removing an object in a body cavity, includes a rotatable drive shaft, a cutter attached to a distal end of the drive shaft and by which the object is cut, a first motor configured to rotate the drive shaft, a microphone configured to collect a sound from the cutter, and a controller configured to control the first motor to rotate the drive shaft based on the sound collected by the microphone.

The medical device control apparatus configured as the above can detect a rotation state of the cutter included in the medical device, and can use the rotation state for the control of the operation of the medical device.

The medical device configured as the above can detect a rotation state of the cutter in the medical device, and can notify an operator of the rotation state.

The medical device configured as the above can detect a state of the cutting by the medical device using the microphone, and can use the state for the control of the medical device.

DESCRIPTION OF THE EMBODIMENTS

Figure 1:
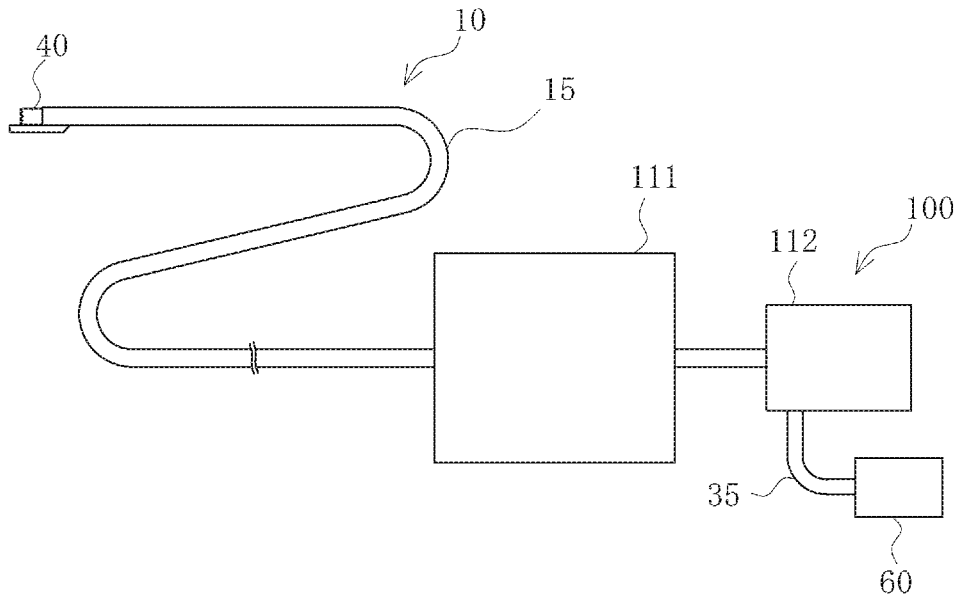
FIG. 1 is a schematic view of a medical operation system including a medical device and a medical device control apparatus in an embodiment.

Hereinafter, embodiments of this disclosure will be described with reference to the drawings. Note that, the size ratios in the drawings may be exaggerated for convenience of explanation, and may be different from the actual ratios in some cases. In the present specification, a side of a medical device 10 to be inserted into a body cavity is referred to as a "distal end" or a "distal side", and an operator-side at which the medical device 10 is operated is referred to as a "proximal end" or a "proximal side".

The medical device 10 according to one embodiment is inserted into a blood vessel, and is used in a procedure of cutting and removing a thrombus, plaque, atheroma, a calcified lesion, and the like, in acute limb ischemia and a deep venous thrombosis. Note that, an object to be removed is not necessarily limited to the thrombus, the plaque, the atheroma, and the calcified lesion, but can be any objects that may exist in a body cavity and in a body lumen.

A medical device control apparatus 100 according to the present embodiment automatically inserts the medical device 10 into a blood vessel of a patient and causes a distal end portion thereof including the cutting unit to reach the vicinity of a lesion area and cut and remove an object in the blood vessel.

Figure 2:
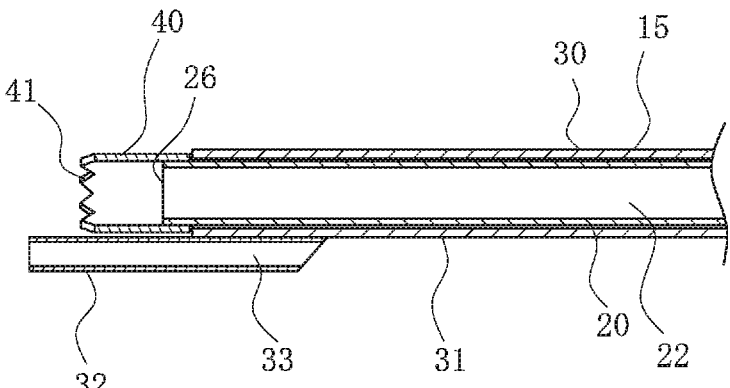
FIG. 2 is an enlarged cross-sectional view of the vicinity of a distal end portion of the medical device.

As illustrated in FIGS. 1 and 2, the medical device 10 includes a shaft portion 15 including an elongated drive shaft 20 that is rotationally driven, and an outer tube 30 that contains the drive shaft 20. A cutting unit 40 serving as a rotating body that cuts an object such as a thrombus is provided in a distal end portion of the drive shaft 20.

The drive shaft 20 transmits a rotation force to the cutting unit 40. In the drive shaft 20, a fluid lumen 22 for transporting a cut object to the proximal side is formed. The drive shaft 20 penetrates through the outer tube 30, and has the distal end portion to which the cutting unit 40 is fixed. The drive shaft 20 includes an inlet portion 26 into which debris (e.g., a cut thrombus or the like) that is an object to be aspirated enters, at the distal end.

The drive shaft 20 is flexible, and has characteristics of allowing the power of rotation acting from the proximal side to be transmitted to the distal side. The drive shaft 20 may include one member as a whole, or may include a plurality of members. The drive shaft 20 may include a spiral-shaped slit or groove to be formed by laser processing or the like, in order to adjust the rigidity thereof depending on a site. Moreover, the distal end portion and the proximal portion of the drive shaft 20 may include different members.

As a constituent material for the drive shaft 20, for example, stainless steel, a shape memory alloy such as a nickel titanium alloy, an alloy (e.g., silver solder component) including silver, copper, zinc, and the like, an alloy (e.g., solder component) including gold, tin, and the like, cemented carbide such as tungsten carbide, polyolefin such as polyethylene and polypropylene, polyamide, polyester such as polyethylene terephthalate, a fluorinated polymer such as tetrafluoroethylene ethylene copolymer (ETFE), polyether ether ketone (PEEK), polyimide, and the like can be used suitably. Moreover, the drive shaft 20 may include a plurality of materials, or a reinforcing member such as a wire rod may be embedded.

The outer tube 30 includes an outer tube main body 31 that contains the drive shaft 20 so as to be rotatable, and a distal end tube 32 that is fixed to a side surface of a distal end portion of the outer tube main body 31.

The distal end portion of the outer tube main body 31 is positioned at a proximal side of the cutting unit 40. The outer tube main body 31 is rotated to allow the cutting unit 40 to be oriented toward an object to be removed. Moreover, the outer tube main body 31 may include a curved portion (not shown) that is bent at a predetermined angle in the distal end portion. The curved portion is rotated together with the outer tube main body 31, and thus can easily cause the cutting unit 40 to contact the object to be removed.

The distal end tube 32 is fixed to an outer peripheral surface of the distal end portion of the outer tube main body 31. The distal end tube 32 includes a distal end lumen 33 into which a guide wire can be inserted. Accordingly, the medical device 10 is a rapid exchange type device in which the distal end lumen 33 through which the guide wire is inserted is formed only in the distal end portion.

Constituent materials for the outer tube main body 31 and the distal end tube 32 are not specially limited, and for example, stainless steel, a shape memory alloy such as a nickel titanium alloy, titanium, an alloy (e.g., silver solder component) including silver, copper, zinc, and the like, an alloy (e.g., solder component) including gold, tin, and the like, cemented carbide such as tungsten carbide, polyolefin such as polyethylene and polypropylene, polyamide, polyester such as polyethylene terephthalate, or various kinds of elastomers, a fluorinated polymer such as ETFE, PEEK, polyimide, polyacetal, and the like, can be used suitably. Moreover, the outer tube main body 31 may include a plurality of materials, or a reinforcing member such as a wire rod may be embedded.

The cutting unit 40 is a cutter that cuts an object such as a thrombus, plaque, or calcified lesion to be small. Accordingly, "cutting" indicates that a force acts on an object to be cut, or an energy acts on such an object, thereby making the object small. An acting method of a force in the cutting, and the shape and form of the object after the cutting are not limited. The cutting unit 40 has a strength enough to cut the above-mentioned object. The cutting unit 40 is fixed to the distal end portion of the drive shaft 20. The cutting unit 40 has a cylinder shape that protrudes to the distal side from the drive shaft 20. The cutting unit 40 is provided with a sharp blade 41 at a distal end thereof. Note that, the shape of the blade 41 is not specially limited. The cutting unit 40 may include not the blade 41 but a large number of minute grinding particles.

A constituent material for the cutting unit 40 preferably has a strength enough to cut a thrombus, and for example, stainless steel, titanium, diamond, ceramics, a shape memory alloy such as a nickel titanium alloy, cemented carbide such as tungsten carbide, an alloy (e.g., silver solder component) including silver, copper, zinc, and the like, high-speed steel, and the like can be used suitably. The constituent material for the cutting unit 40 may be resin such as polyether ether ketone (PEEK), or engineering plastic such as polyacetal.

The medical device control apparatus 100 includes a first operation unit 111 by which forward-and-rearward and rotary motions of the medical device 10 are controlled, and a second operation unit 112 by which rotation and aspiration of the cutting unit 40 serving as a rotating body of the medical device 10 are controlled. The first operation unit 111 and the second operation unit 112 can be connected to each other via one or more wires through which control signals from a control unit 125 (described later) are conveyed and electric power is supplied.

Figure 3:
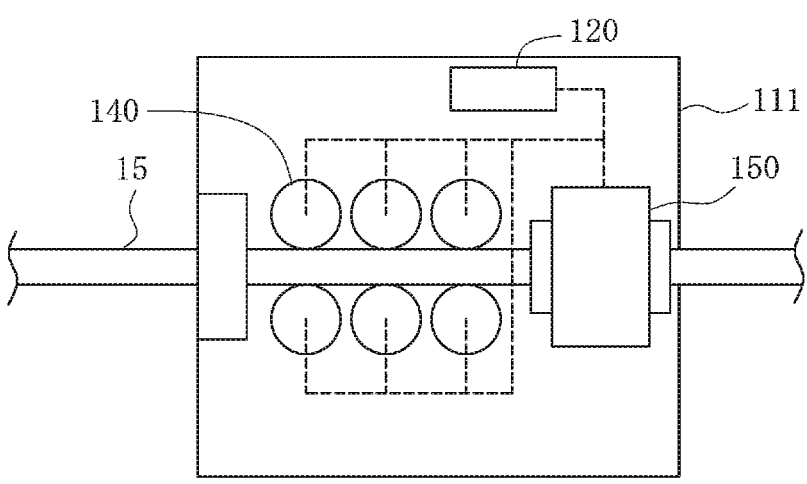
FIG. 3 is an enlarged schematic view of a first operation unit of the medical device control apparatus.

As illustrated in FIG. 3, the shaft portion 15 is inserted through the first operation unit 111, and the first operation unit 111 includes an axial direction driving unit 140 including a plurality of rollers that move the shaft portion 15 along its axial direction, and a circumferential direction driving unit 150 such as a roller that surrounds the shaft portion 15 and rotates the shaft portion 15 along its circumferential direction. That is, the rotation axes of the axial direction driving unit 140 are perpendicular to the axis of the shaft portion 15, and the rotation axis of the circumferential direction driving unit 150 coincides with the axis of the shaft portion 15. The axial direction driving unit 140 and the circumferential direction driving unit 150 are connected to a device operation unit 120 serving as a drive source of these respective driving units via one or more shafts and gears. The device operation unit 120 includes, for example, an electric motor, but is not limited thereto as long as it can drive the axial direction driving unit 140 and the circumferential direction driving unit 150.

Figure 4:
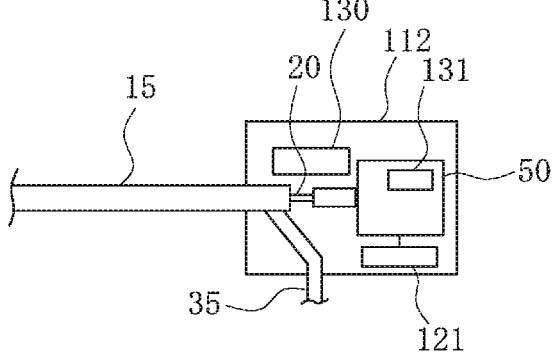
FIG. 4 is an enlarged schematic view of a second operation unit of the medical device control apparatus.

As illustrated in FIG. 4, a proximal portion of the shaft portion 15 is inserted through the second operation unit 112. Inside of the second operation unit 112, the drive shaft 20 of the shaft portion 15 is exposed, and is connected to a rotation drive source 50. The rotation drive source 50 can include an electric motor. In the second operation unit 112, a drive operation unit 121 such as a control circuit that performs an on-and-off operation and controlling the rotational frequency of the rotation drive source 50 is provided. Inside of the second operation unit 112, the shaft portion 15 is bifurcated, and a bifurcated tube 35 after the bifurcation is connected to an aspiration drive source 60. The aspiration drive source 60 can include a pump.

Inside of the second operation unit 112, a device detection unit 126 for detecting a rotation state of the cutting unit 40 serving as a rotating body is provided. As the device detection unit 126, provided are a sound collection microphone 130 that is disposed in the vicinity of the rotation drive source 50, and a temperature sensor 131 that detects a temperature of the rotation drive source 50. The sound collection microphone 130 can collect sound emitted by the rotation drive source 50. The temperature sensor 131 can include, for example, a thermocouple sensor or an infrared ray sensor that measures the temperature of the rotation drive source 50 by being in contact or non-contact with the rotation drive source 50.

The device detection unit 126 is not limited to the aforementioned configuration and arrangement as long as it can detect a state of the medical device 10. The device detection unit 126 may detect, in addition to the drive sound of the rotation drive source 50, the rotational frequency of the drive shaft 20, a cutting sound that is generated with the cutting, a value of a current that is supplied to the rotation drive source 50, and the like. As the device detection unit 126, for example, a rotation detection sensor capable of optically detecting a rotational frequency or detecting a magnetic field may be used to detect the rotational frequency of the drive shaft 20. Moreover, the device detection unit 126 can measure a reaction force to be received with the cutting of the rotation drive source 50. Moreover, the device detection unit 126 can be disposed in various places if necessary. For example, the device detection unit 126 can also be disposed, in addition to the inside of the second operation unit 112, inside of the first operation unit 111, the shaft portion 15, the aspiration drive source 60 or the vicinities thereof, or can also be disposed to the living body by adhesion.

Figure 5:
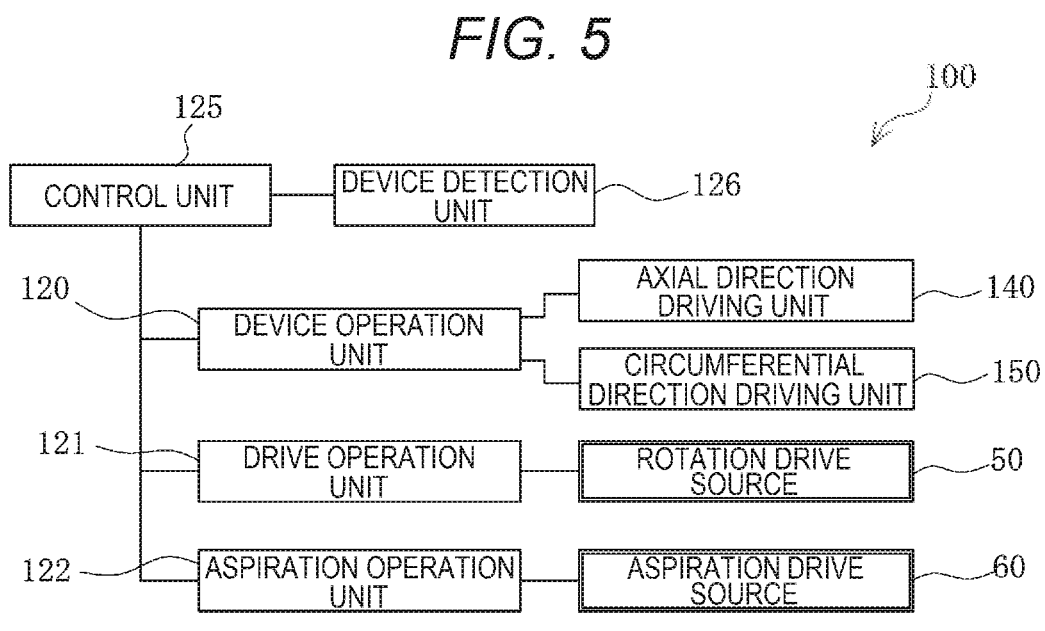
FIG. 5 is a hardware block diagram of the medical device control apparatus.

As illustrated in FIG. 5, the medical device control apparatus 100 includes a control unit 125 such as a control circuit or a controller that controls the device operation unit 120, the drive operation unit 121, and an aspiration operation unit 122. The control unit 125 is disposed in the first operation unit 111, the second operation unit 112, or an external device (not shown). The device detection unit 126 is connected to the control unit 125. As mentioned in the foregoing, the device operation unit 120 (e.g., a motor) drives the axial direction driving unit 140 and the circumferential direction driving unit 150 to control forward-and-rearward and circumferential motions of the medical device 10. Moreover, the drive operation unit 121 (e.g., a control circuit) controls the rotation drive source 50 of the medical device 10, and the aspiration operation unit 122 such as a control circuit that controls the aspiration drive source 60 of the medical device 10. Note that, in FIG. 5, the configuration in the medical device 10 is illustrated by being surrounded by the double line.

The control unit 125 includes, for example, a processor such as a central processing unit (CPU) or a micro processing unit (MPU), and a storage unit such as a memory. The control unit 125 executes a program stored in the storage unit to control the medical device 10.

Figure 6:
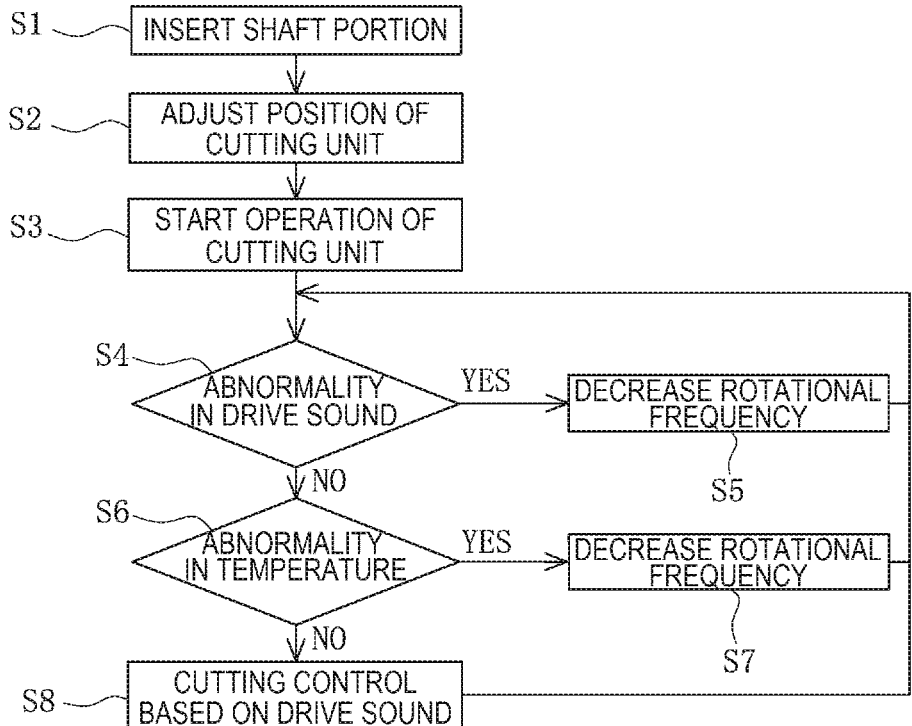
FIG. 6 is a flowchart of operation control performed by the medical device control apparatus.

The operation control of the medical device 10 by the control unit 125 will be described. As illustrated in FIG. 6, the shaft portion 15 is inserted into a blood vessel (S1). In order to insert the shaft portion 15 into the blood vessel, the guide wire is firstly inserted into the vicinity of a lesion area. The control unit 125 controls the drive operation unit 120 to insert the shaft portion 15 into the blood vessel and move it toward the lesion area along the guide wire in a state in which the guide wire passes through the distal end lumen 33 of the shaft portion 15.

When the cutting unit 40 has reached the vicinity of the lesion area, the control unit 125 adjusts an axial direction position and a circumferential direction position of the shaft portion 15 by the device operation unit 120 (S2). After having adjusted the cutting unit 40 to a position at which the lesion area can be cut, the control unit 125 starts the rotation of the rotation drive source 50 by the drive operation unit 121, and starts the operation of the cutting unit 40 (S3).

The control unit 125 detects whether there is an abnormality in a drive sound of the rotation drive source 50 collected by the sound collection microphone 130 included in the device detection unit 126 during when the cutting unit 40 is operating (S4). The abnormality in the drive sound occurs in a case where the cutting unit 40 is not normally in contact with the lesion area, a case where the lesion area is hard and cannot be cut by the cutting unit 40, and other cases. Whether an abnormality is present in the drive sound can be detected, for example, from the frequency of the sound emitted by the rotation drive source 50, a cycle of the frequency variation, and the like. If an abnormality in the drive sound has been detected at S4, the control unit 125 causes the drive operation unit 121 to decrease the rotational frequency of the rotation drive source 50 (S5). Note that, if an abnormality in the drive sound has been detected, the control unit 125 may stop the rotation drive source 50.

Moreover, the control unit 125 detects whether an abnormality is present in the temperature of the rotation drive source 50 measured by the temperature sensor 131 included in the device detection unit 126 during when the cutting unit 40 is operating (S6). Detecting the temperature abnormality in the rotation drive source 50 enables an abnormality in a value of a current that is supplied to the rotation drive source 50 to be detected. If an abnormality in the temperature has been detected at S6, the control unit 125 causes the drive operation unit 121 to decrease the rotational frequency of the rotation drive source 50 (S7). Note that, if an abnormality in the temperature has been detected, the control unit 125 may stop the rotation drive source 50.

If an abnormality is neither present in the drive sound nor the temperature, the control unit 125 controls the cutting by the cutting unit 40 based on the drive sound of the rotation drive source 50 collected by the sound collection microphone 130 (S8). When the cutting unit 40 cuts the lesion area, the drive sound emitted by the rotation drive source 50 changes depending on a cutting situation, so that the control unit 125 can efficiently conduct the cutting of the lesion area by grasping the cutting situation from the drive sound of the rotation drive source 50 collected by the sound collection microphone 130, and controlling the rotation drive source 50 to be a more suitable rotational frequency. Moreover, the sound collection microphone 130 can detect a state of the medical device 10 in a non-contact manner, so that even if the medical device 10 does not correspond to the medical device control apparatus 100, it is possible to detect a state of the medical device 10 at the medical device control apparatus 100 side.

The control unit 125 can move the shaft portion 15 in a proximal direction by the device operation unit 120 when a certain period of time has passed after the rotation state of the cutting unit 40 detected by the device detection unit 126 was changed not less than a certain level, and can move the shaft portion 15 in a distal end direction by the device operation unit 120 when a certain period of time has further passed after this movement. Moreover, the control unit 125 can repeat this operation a plurality of times. Accordingly, it is possible to repeat the contact and the separation of the cutting unit 40 with respect to the lesion area, and to efficiently advance the cutting of the lesion area.

The drive operation unit 121 may be detachable from the second operation unit 112 and used for another medical device.

Figure 7:
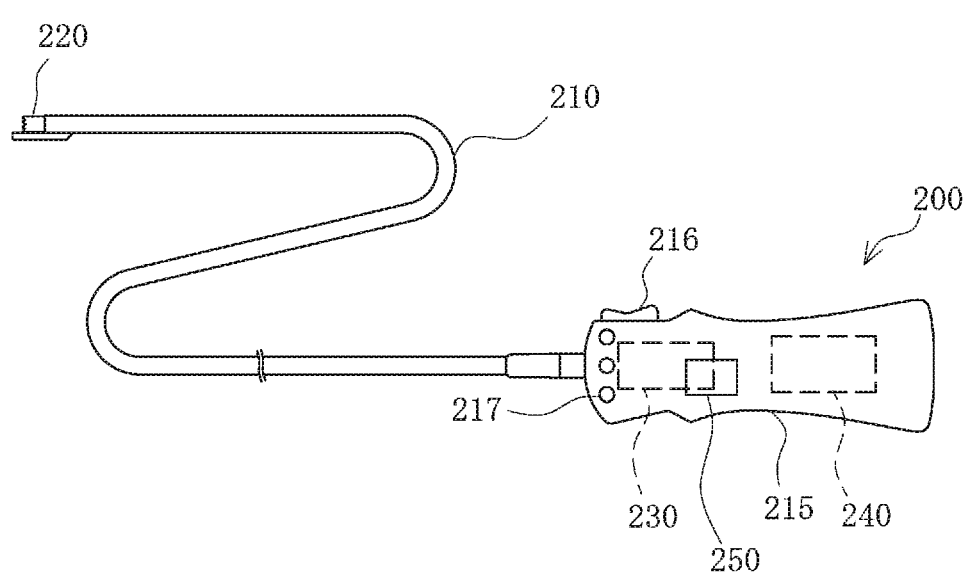
FIG. 7 is a schematic view of a medical device in a second embodiment.

Next, a second embodiment of this disclosure will be described. As illustrated in FIG. 7, a medical device 200 according to the second embodiment includes a cutting unit 220 serving as a rotating body that is provided in a distal end portion of an elongated shaft portion 210, and a handle portion 215 that is gripped and operated by a hand of an operator in a proximal portion of the shaft portion 210. Inside of the handle portion 215, a rotation drive source 230 and an aspiration drive source 240 are disposed. Moreover, in the handle portion 215, an operation switch 216 for controlling the rotation, the aspiration, and the like of the cutting unit 220, and a notification unit 217 for notifying the operator of the state of the cutting. The notification unit 217 includes a plurality of lamps such as LEDs, and can indicate the state of the cutting in the cutting. Note that, the notification unit 217 may have another configuration as long as it can make a notification of the state of the cutting, and for example, a display screen, a speaker that generates a sound, and the like may be employed.

In the handle portion 215, a sound collection microphone 250 serving as a device detection unit is provided at a vicinity position of the rotation drive source 230. The sound collection microphone 250 can collect a drive sound of the rotation drive source 230 that operates the cutting unit 220.

Figure 8:
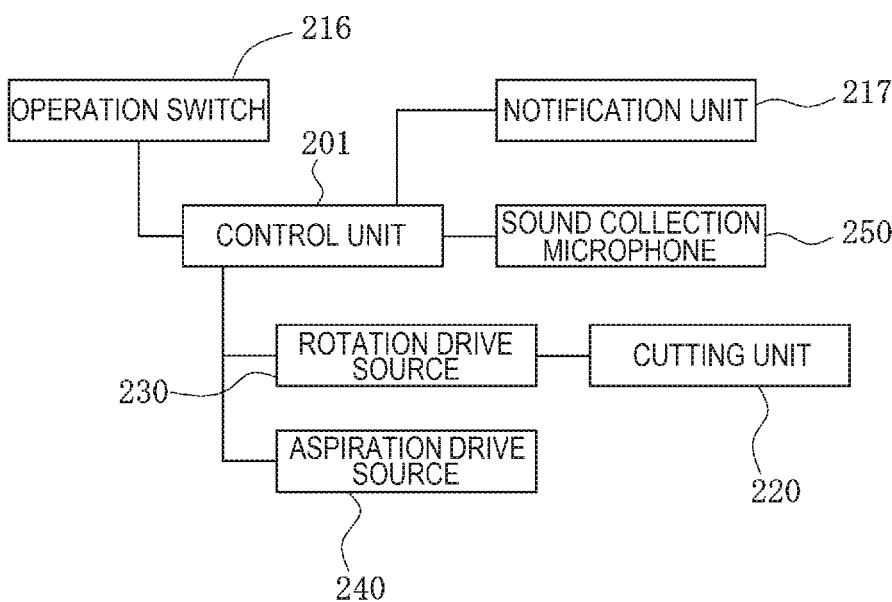
FIG. 8 is a hardware block diagram of the medical device in the second embodiment.

As illustrated in FIG. 8, the medical device 200 includes a control unit 201 such as a control circuit or a controller that controls the rotation drive source 230 and the aspiration drive source 240. The operation switch 216, the sound collection microphone 250 serving as a device detection unit, and the notification unit 217 are connected to the control unit 201.

When the control unit 201 has caused the cutting unit 220 to rotate by the rotation drive source 230, the control unit 201 determines a cutting state of the cutting unit 220 based on a drive sound from the rotation drive source 230 collected by the sound collection microphone 250, and causes the notification unit 217 to make a notification based on the determination. Examples of the cutting state include a state where the cutting is normally performed (e.g., when the same sound are constantly collected), a state where the cutting is not performed because the cutting unit 220 does not come into contact with the lesion area, for example, and a state where the cutting unit 220 cannot perform the cutting because the lesion area is hard, and the control unit 201 identifies states from these drive sounds, and makes a different notification (e.g., different color or pattern of light) in accordance with the state. Accordingly, the operator can recognize the cutting state, and can conduct a more suitable operation of the medical device 10.

The medical device 200 can includes a sensor such as an ultrasound sensor that acquires a cross-sectional image of the lesion area, and a display unit (e.g., an external monitor) that displays the cross-sectional image acquired by the image sensor. In this case, as device detection units, in addition to the sound collection microphone 250, a temperature sensor that detects a temperature of the rotation drive source 230, a camera that faces the display unit and detects the luminance of the cross-sectional image acquired by the image sensor and displayed on the display unit can be provided. In the cross-sectional image displayed on the display unit, the luminance of the lesion area portion becomes high in a case where the lesion area is hard. At this time, the drive sound of the rotation drive source 230 to be acquired by the sound collection microphone 250 becomes louder, and the temperature of the rotation drive source 230 acquired by the temperature sensor also becomes higher. Thus, it is possible to generate a trained model using a machine learning technique to determine whether the lesion area can be cut using these information and a cutting enabled state of an actual lesion area as training data. The control unit 201 can determine, using the generated model, a cutting possibility of the lesion area from the sound emitted by the medical device 200, the temperature of the rotation drive source 230, and the luminance of the cross-sectional image to be displayed on the display unit, acquired by the device detection unit, and can cause the notification unit 217 to make a notification of the inferred cutting possibility of the lesion area. Therefore, it is possible to provide the useful information to the operator.

As is in the foregoing, the medical device control apparatus 100 according to the present embodiment includes: the second operation unit 112 that controls the medical device 10 including the elongated shaft portion 15, the cutting unit 40 that is provided in the distal end portion of the shaft portion 15, and the rotation drive source 50 that rotates the cutting unit 40; and the device detection unit 126 that is disposed in the second operation unit 112, and detects a state of the medical device 10 including at least a rotation state of the cutting unit 40. The medical device control apparatus 100 configured in this manner can detect a rotation state of the cutting unit 40 included in the medical device 10 by the medical device control apparatus 100, and can use the rotation state for the control of the medical device 10.

Moreover, the device detection unit 126 may detect the rotation state of the cutting unit 40 in a non-contact manner.

Accordingly, the device detection unit 126 can be retrofitted to the medical device 10, and can detect a situation of the cutting unit 40 even in the medical device 10 that does not support the medical device control apparatus 100.

Moreover, the device detection unit 126 may include the sound collection microphone 130 that is disposed in the vicinity of the rotation drive source 50. Accordingly, it is possible to detect a cutting state from the drive sound of the rotation drive source 50.

Moreover, the device detection unit 126 may include the temperature sensor 131 that detects a temperature of the rotation drive source 50. Accordingly, it is possible to detect a cutting state from the temperature of the rotation drive source.

Moreover, the device detection unit 126 may include a rotation detection sensor that detects a rotational frequency of the cutting unit 40. Accordingly, it is possible to detect a cutting state from the rotational frequency of the cutting unit 40.

Moreover, the control unit 125 controls the rotation drive source 50 based on the rotation state of the cutting unit 40 detected by the device detection unit 126. Accordingly, it is possible to reliably control the rotation drive source 50.

Moreover, the control unit 125 may move the shaft portion 15 in a proximal direction by the first operation unit 111 when a certain period of time has passed after the rotation state of the cutting unit 40 detected by the device detection unit 126 was changed not less than a certain level, and may move the shaft portion 15 in a distal end direction by the first operation unit 111 when a certain period of time has passed from the movement. Accordingly, it is possible to repeat the contact and the separation of the cutting unit 40 with respect to the lesion area, and to efficiently advance the cutting of the lesion area.

Moreover, the drive operation unit 121 may be detachable from the second operation unit 112. Accordingly, it is possible to share the drive operation unit 121 with the second operation unit 112 of another medical device control apparatus 100.

Moreover, the medical device 200 according to the second embodiment includes: the elongated shaft portion 210, the cutting unit 220 that is provided in a distal end portion of the shaft portion 210; the rotation drive source 230 that rotates the cutting unit 220; and the handle portion 215 that is provided in a proximal portion of the shaft portion 210, in which the sound collection microphone 250, the control unit 201, and the notification unit 217 are provided in the handle portion 215, the device detection unit detects a state of the medical device 200 including at least a rotation state of the cutting unit 220, and the control unit 201 causes the notification unit 217 to make a notification of information based on the rotation state of the cutting unit 220 detected by the device detection unit. The medical device 200 configured in this manner can detect a rotation state of the cutting unit 220 in the medical device 200, and can notify an operator of the rotation state.

Moreover, an image sensor that acquires a cross-sectional image of a lesion area, and a display unit that displays the cross-sectional image acquired by the image sensor may be provided; the device detection unit may detect at least a sound to be emitted by the medical device 200, a temperature of the rotation drive source 230, and a luminance of the cross-sectional image to be displayed on the display unit; and the control unit 201 may determine, using a trained model, a cutting possibility of the lesion area from the sound to be emitted by the medical device 200, the temperature of the rotation drive source 230, and the luminance of the cross-sectional image to be displayed on the display unit, acquired by the device detection unit, and may cause the notification unit 217 to make a notification of the determined cutting possibility of the lesion area. Accordingly, it is possible to provide useful information when the operator advances the procedure.

Moreover, the medical device 200 according to the second embodiment includes: the elongated shaft portion 210; the cutting unit 220 that is provided in a distal end portion of the shaft portion 210; the rotation drive source 230 that drives the cutting unit 220; the control unit 201 that controls the rotation drive source 230, and the sound collection microphone 250 that detects a cutting state by the cutting unit 220. The sound collection microphone 350 may be disposed at the cutting unit 220 or the rotation drive source 230 to detect a cutting state by the cutting unit 220. The medical device 200 configured in this manner can detect a state of the cutting by the medical device 200 using the sound collection microphone 250, and can use the detected state for the control of the medical device 200.

Moreover, the control unit 201 that controls the rotation drive source 230 may be provided, and the control unit 201 may control the rotation drive source 230 based on the cutting state by the cutting unit detected by the sound collection microphone 250. Accordingly, it is possible to reliably control the rotation drive source 230 or the cutting unit 220.

Note that, this disclosure is not limited to the above-described embodiments, and various changes by those skilled in the art can be made within the technical scope of this disclosure.

In the above-mentioned embodiments, the medical devices 10 and 200 detect a state of the cutting units 40 and 220 by the device detection unit, but a device detection unit that detects a state of another unit other than the cutting units 40 and 220 may be provided. For example, in a case where the medical device 10 or 200 includes a laser irradiation unit as a cutting unit, the medical device 10 or 200 may include a device detection unit capable of detecting a state of the laser irradiation unit. The laser to be emitted by the laser irradiation unit is generated by a laser oscillator that is provided in a hand-side portion (e.g., e.g., the handle portion 215) and serves as the cutting driving unit, and a sound collection microphone that is disposed in the vicinity the laser oscillator can serve as a device detection unit that collects the sound from the laser oscillator. In a case where a cutting state by the laser irradiation unit can be identified based on the sound from the laser oscillator collected by the sound collection microphone, the control unit can control the laser oscillator based on information on the cutting state.

While certain embodiments have been described, these embodiments have been presented by way of example only, and are not intended to limit the scope of the disclosure. Indeed, the novel embodiments described herein may be embodied in a variety of other forms; furthermore, various omissions, substitutions and changes in the form of the embodiments described herein may be made without departing from the spirit of the disclosure. The accompanying claims and their equivalents are intended to cover such forms or modifications as would fall within the scope and spirit of the disclosure.

What is claimed is:

1. A medical device control apparatus for controlling a medical device configured to remove an object in a body cavity with a cutter that is rotatable via a rotatable drive shaft, the apparatus comprising:

a first motor configured to rotate the drive shaft;

one or more sensors configured to detect a state of the first motor; and a controller configured to control the first motor to rotate the drive shaft based on the state of the first motor detected by the one or more sensors, wherein the one or more sensors include a microphone disposed in a vicinity of the first motor and configured to collect a sound therefrom.

2. The medical device control apparatus according to claim 1, wherein the one or more sensors detect the state of the first motor in a non-contact manner.

3. The medical device control apparatus according to claim 1, wherein the one or more sensors include a temperature sensor configured to detect a temperature of the first motor.

4. The medical device control apparatus according to claim 1, wherein the one or more sensors include an optical sensor configured to detect a rotational frequency of the first motor.

5. The medical device control apparatus according to claim 1, further comprising:

a second motor that drives one or more rollers to move the drive shaft along an axial direction thereof, and the controller is further configured to drive the second motor based on the state of the first motor.

6. The medical device control apparatus according to claim 5, wherein the controller controls the second motor to move the drive shaft towards a proximal side when the state of the first motor has not changed for a certain period of time, and then move the drive shaft towards a distal side after a certain period of time.

7. The medical device control apparatus according to claim 5, wherein the second motor is further configured to drive another roller to rotate an outer tube surrounding the drive shaft to change an orientation thereof.

8. The medical device control apparatus according to claim 5, further comprising:

a first housing through which the drive shaft passes and in which the second motor is housed.

9. The medical device control apparatus according to claim 8, further comprising:

a second housing in which the first motor, the one or more sensors, and the controller are housed, wherein a proximal end of the drive shaft is connected to the first motor in the second housing, and the first housing is between the cutter and the second housing.

10. A medical device for removing an object in a body cavity, comprising:

a rotatable drive shaft;

a cutter attached to a distal end of the drive shaft and by which the object is cut;

a first motor configured to rotate the drive shaft;

one or more sensors configured to detect a state of the first motor; and a controller configured to issue a notification signal based on the state of the first motor detected by the one or more sensors, wherein the one or more sensors include a microphone disposed in a vicinity of the first motor and configured to collect a sound therefrom.

11. The medical device according to claim 10, further comprising:

a handle portion in which the drive shaft is connected to the first motor and the one or more sensors are disposed.

12. The medical device according to claim 11, further comprising:

one or more lamps along an outer surface of the handle portion and configured to emit light in response to the notification signal.

13. The medical device according to claim 10, wherein the one or more sensors include a temperature sensor configured to detect a temperature of the first motor.

14. The medical device according to claim 13, further comprising:

an image sensor configured to acquire a cross-sectional image of a lesion area inside the body cavity; and a display configured to display the cross-sectional image of the lesion area acquired by the image sensor, wherein the one or more sensors include a camera configured to detect a luminance of the cross-sectional image of the lesion area displayed on the display, and the controller is further configured to use a machine learning model that has been trained to determine a cutting possibility of the lesion area corresponding to the sound collected by the microphone, the temperature detected by the temperature sensor, and the luminance of the cross-sectional image of the lesion area detected by the camera.

15. A medical device for removing an object in a body cavity, comprising:

a rotatable drive shaft;

a cutter attached to a distal end of the drive shaft and by which the object is cut;

a first motor configured to rotate the drive shaft;

a microphone configured to collect a sound from the first motor; and a controller configured to control the first motor to rotate the drive shaft based on the sound collected by the microphone.

16. The medical device according to claim 15, further comprising:

a temperature sensor configured to detect a temperature of the first motor, wherein the controller controls the first motor further based on the temperature detected by the temperature sensor.

17. A medical device for removing an object in a body cavity, comprising:

a rotatable drive shaft;

a cutter attached to a distal end of the drive shaft and by which the object is cut;

a first motor configured to rotate the drive shaft;

a microphone configured to collect a sound from the cutter; and a controller configured to control the first motor to rotate the drive shaft based on the sound collected by the microphone.

18. The medical device according to claim 17, further comprising:

a temperature sensor configured to detect a temperature of the first motor, wherein the controller controls the first motor further based on the temperature detected by the temperature sensor.

* * * * *